United States Patent
Kelly

(10) Patent No.: US 10,596,232 B2
(45) Date of Patent: Mar. 24, 2020

(54) METHODS AND COMPOSITIONS RELATED TO LONG HALF-LIFE COAGULATION COMPLEXES

(71) Applicant: CELL MACHINES, INC., Houston, TX (US)

(72) Inventor: James Kelly, Houston, TX (US)

(73) Assignee: Cell Machines, Inc., Houston, TX (US)

( * ) Notice: Subject to any disclaimer, the term of this patent is extended or adjusted under 35 U.S.C. 154(b) by 0 days.

(21) Appl. No.: 15/751,239

(22) PCT Filed: Aug. 10, 2016

(86) PCT No.: PCT/US2016/046264
§ 371 (c)(1),
(2) Date: Feb. 8, 2018

(87) PCT Pub. No.: WO2017/027545
PCT Pub. Date: Feb. 16, 2017

(65) Prior Publication Data
US 2018/0228872 A1    Aug. 16, 2018

Related U.S. Application Data

(60) Provisional application No. 62/203,973, filed on Aug. 12, 2015.

(51) Int. Cl.
*A61K 38/36* (2006.01)
*A61K 38/37* (2006.01)
(Continued)

(52) U.S. Cl.
CPC .............. *A61K 38/37* (2013.01); *A61K 38/36* (2013.01); *A61K 38/48* (2013.01);
(Continued)

(58) Field of Classification Search
CPC ........ A61K 38/37; A61K 47/62; A61K 47/64; A61K 47/643; A61K 38/4846;
(Continued)

(56) References Cited

U.S. PATENT DOCUMENTS 4,002,531 A   1/1977   Royer
5,349,052 A   9/1994   Delgado et al.
(Continued)

FOREIGN PATENT DOCUMENTS

EP    0401384    12/1990
WO    95/06058    3/1995
(Continued)

OTHER PUBLICATIONS

Andersen, J. T., et al., (2011). Extending half-life by indirect targeting of the neonatal Fc receptor (FcRn) using a minimal albumin binding domain. The Journal of Biological Chemistry, 286(7), 5234-5241. Retrieved from http://www.jbc.org/content/286/7/5234.full.pdf+html.
(Continued)

*Primary Examiner* — Jeffrey E. Russel
(74) *Attorney, Agent, or Firm* — Meunier Carlin & Curfman LLC

(57) ABSTRACT

Disclosed herein are methods and compositions related to coagulation factor complexes comprising a coagulation factor; a fusion protein; and a modifying molecule, wherein the modifying molecule is coupled to the coagulation factor in such a way as to allow binding by the fusion protein, thereby creating a modified coagulation factor; wherein the modified coagulation factor and the fusion protein interact in at least two independent sites.

23 Claims, 11 Drawing Sheets

Scheme for construction of long half life FVIII

(51) Int. Cl.
- A61K 38/48 (2006.01)
- A61K 47/62 (2017.01)
- A61K 47/64 (2017.01)
- C07K 14/745 (2006.01)
- C07K 14/755 (2006.01)
- C07K 19/00 (2006.01)
- C12N 9/64 (2006.01)
- A61P 7/04 (2006.01)

(52) U.S. Cl.
CPC .......... *A61K 38/4846* (2013.01); *A61K 47/62* (2017.08); *A61K 47/64* (2017.08); *A61K 47/643* (2017.08); *A61P 7/04* (2018.01); *C07K 14/745* (2013.01); *C07K 14/755* (2013.01); *C12N 9/6437* (2013.01); *C12Y 304/21021* (2013.01); *C07K 2319/31* (2013.01); *C07K 2319/70* (2013.01)

(58) Field of Classification Search
CPC ............ A61K 38/36–37; C07K 14/755; C07K 2319/31; C07K 14/2319; C07K 14/31; C07K 14/70; C07K 14/745–755; C07K 2319/70; C12N 9/6437
See application file for complete search history.

(56) References Cited

U.S. PATENT DOCUMENTS

| | | | |
|---|---|---|---|
| 5,612,460 | A | 3/1997 | Zalipsky |
| 5,643,575 | A | 7/1997 | Martinez et al. |
| 2011/0040073 | A1 | 2/2011 | Ostergaard et al. |
| 2012/0148557 | A1 | 6/2012 | Kronthaler |
| 2012/0190096 | A1* | 7/2012 | Siekmann ............ A61K 47/542 435/188 |
| 2015/0023959 | A1 | 1/2015 | Chhabra et al. |

FOREIGN PATENT DOCUMENTS

| | | |
|---|---|---|
| WO | 98/32466 | 7/1998 |
| WO | 2008077616 | 7/2008 |
| WO | 2011/101277 A1 | 8/2011 |
| WO | 2011101284 | 8/2011 |
| WO | 2012/087838 A1 | 6/2012 |
| WO | 2013106787 | 7/2013 |
| WO | 2013/120939 A1 | 8/2013 |
| WO | 2014011819 | 3/2014 |
| WO | 2014173873 | 10/2014 |
| WO | 2014/210547 A1 | 12/2014 |

OTHER PUBLICATIONS

Ausubel, F. M. et al., (1989). Current protocol in Molecular Biology, Green publishing associates, Inc., and John Wiley & Sons Inc., New York, at pp. 6.3.1-6.3.6 and 2.10.3.

Bradbury, A. R. M., et al., (2011). Beyond natural antibodies: the power of in vitro display technologies. Nature Publishing Group, 29(3), 245-254. http://doi.org/10.1038/nbt.1791.

Brutlag et al., (1990). Improved sensitivity of biological sequence database searches. Comp. App. Biosci. 6:237-245.

Buyue, Y., et al. (2014). A Single Chain Variant of Factor VIII Fc Fusion Protein Retains Normal In Vivo Efficacy but Exhibits Altered In Vitro Activity. PLoS ONE, 9(11), e113600. http://doi.org/10.1371/journal.pone.0113600.

Caliceti et al., (1999). Biopharmaceutical Properties of Uricase Conjugated to Neutral and Amphiphilic Polymers. Bioconjug. Chem. 10:638-646.

Delgado et al., (1992). Crit. Rev. Thera. Drug Carrier Sys. 9:249-304.

Dobeli et al., (1988). Role of the carboxy-terminal sequence on the biological activity of human immune interferon (IFN-γ). J. Biotechnology 7:199-216.

Francis et al., (1998). PEGylation of cytokines and other therapeutic proteins and peptides: the importance of biological optimisation of coupling techniques. Intern. J. of Hematol. 68:1-18.

Ginn, C., et al., (2014). PEGylation and its impact on the design of new protein-based medicines. Future Medicinal Chemistry, 6(16), 1829-1846. http://doi.org/10.4155/fmc.14.125.

Hoots, W. K. (2003). Comprehensive care for hemophilia and related inherited bleeding disorders: why it matters. Current Hematology Reports, 2(5), 395-401.

Kelly, J. H., & Sussman, N. L. (2000). A Fluorescent Cell-Based Assay for Cytochrome P-450 Isozyme 1A2 Induction and Inhibition. Journal of Biomolecular Screening, 5(4), 249-253. http://doi.org/10.1177/108705710000500407.

Kempton, C. L., & Meeks, S. L. (2014). Toward optimal therapy for inhibitors in hemophilia. Hematology / the Education Program of the American Society of Hematology. American Society of Hematology. Education Program, 2014(1), 364-371. http://doi.org/10.1182/asheducation-2014.1.364.

Kramer, R. H., & Karpen, J. W. (1998). Spanning binding sites on allosteric proteins with polymer-linked ligand dimers. Nature, 395(6703), 710-713. http://doi.org/10.1038/27227.

Lawson, J. H., Butenas, S., Ribarik, N., & Mann, K. G. (1993). Complex-dependent inhibition of factor VIIa by antithrombin III and heparin. The Journal of Biological Chemistry, 268(2), 767-770.

Lenting, P. J., Christophe, O. D., & Denis, C. V. (2015). von Willebrand factor biosynthesis, secretion, and clearance: connecting the far ends. Blood, 125(13), 2019-2028. http://doi.org/10.1182/blood-2014-06-528406.

Malik et al., (1992). Polyethylene glycol (PEG)-modified granulocyte-macrophage colony-stimulating factor (GM-CSF) with conserved biological activity. Exp. Hematol. 20:1028-1035.

Mannucci, P. M., & Mancuso, M. E. (2014). Fc-fusion technology and recombinant FVIII and FIX in the management of the hemophilias. Drug Design, Development and Therapy, 365. http://doi.org/10.2147/DDDT.S47312.

Mei, B., Pan, C., Jiang, H., Tjandra, H., Strauss, J., Chen, Y., et al. (2010). Rational design of a fully active, long-acting PEGylated factor VIII for hemophilia A treatment. Blood, 116(2), 270-279. http://doi.org/10.1182/blood-2009-11-254755.

Morpurgo et al., (1996). Covalent modification of mushroom tyrosinase with different amphiphic polymers for pharmaceutical and biocatalysis applications Appl. Biochem. Biotechnol. 56:59-72.

Oldenburg, J., & Albert, T. (2014). Novel products for haemostasis—current status. Haemophilia, 20, 23-28. http://doi.org/10.1111/hae.12428.

Orlova, N. A., Kovnir, S. V., Vorobiev, I. I., Gabibov, A. G., & Vorobiev, A. I. (2013). Blood Clotting Factor VIII: From Evolution to Therapy. Acta Naturae, 5(2), 19-39.

Pasut, G., & Veronese, F. M. (2012). State of the art in PEGylation: The great versatility achieved after forty years of research. Journal of Controlled Release, 161(2), 461-472.

Philips, J.-C., & Scheen, A. (2006). Insulin detemir in the treatment of type 1 and type 2 diabetes. Vascular Health and Risk Management, 2(3), 277-283.

Pipe, S. W. (2010). Hemophilia: new protein therapeutics. Hematology / the Education Program of the American Society of Hematology. American Society of Hematology. Education Program, 2010, 203-209. http://doi.org/10.1182/asheducation-2010.1.203.

Powell et al., Novel Approaches for Hemophilia Treatment. Mar. 19, 2015. Accessed on-line at: http://www.medscape.com/viewarticle/841623_5.

Ran, F. A., Hsu, P. D., Lin, C.-Y., Gootenberg, J. S., Konermann, S., Trevino, A. E., et al. (2013). Double Nicking by RNA-Guided CRISPR Cas9 for Enhanced Genome Editing Specificity. Cell, 1-15. http://doi.org/10.1016/j.cell.2013.08.021.

Rattan et al., (1992) Protein Synthesis, Posttranslational Modifications, and Aginga. Ann. N.Y. Acad. Sci. 663:48-62.

Ron et al. (1993). J. Biol. Chem. 268: 2984-2988.

Schulte et al., (2013). Innovative coagulation factors: albumin fusion technology and recombinant single-chain factor VIII. Thromb Res. 131 Suppl 2: S2-S6.

(56) References Cited

OTHER PUBLICATIONS

Schulte, S. (2008). Use of albumin fusion technology to prolong the half-life of recombinant factor VIIa. Thrombosis Research, 122(S4), S14-S19. http://doi.org/10.1016/S0049-3848(08)70029-X.
Seifter et al., (1990). Analysis for protein modifications and non-protein cofactors Meth. Enzymol. 182:626-646.
Shapiro et al., Long-lasting recombinant factor VIII proteins for hemophilia A. ASH Education Book Dec. 6, 2013 vol. 2013 No. 1 37-43 (Review Article).
Smith, S. A., Travers, R. J., & Morrissey, J. H. (2015). How it all starts: Initiation of the clotting cascade. Critical Reviews in Biochemistry and Molecular Biology, 50(4): 326-336. http://doi.org/10.3109/10409238.2015.1050550.
Srivastava, A., Brewer, A. K., Mauser-Bunschoten, E. P., Key, N. S., Kitchen, S., Llinas, A., et al. (2012). Guidelines for the management of hemophilia. Haemophilia, 19(1), e1-e47. http://doi.org/10.1111/j.1365-2516.2012.02909.x.
Stennicke, H. R., Kjalke, M., Karpf, D. M., Balling, K. W., Johansen, P. B., Elm, T., et al. (2013). A novel B-domain O-glycoPEGylated FVIII (N8-GP) demonstrates full efficacy and prolonged effect in hemophilic mice models. Blood, 121(11), 2108-2116. http://doi.org/10.1182/blood-2012-01-407494.
Swystu, et al., FVIII stabilization: VWF D'D3 Will Do. Blood 2014 124:313-315.
Vadivel, K., & Bajaj, S. P. (2012). Structural biology of factor VIIa/tissue factor initiated coagulation. Frontiers in Bioscience: a Journal and Virtual Library, 17, 2476-2494.
Van der Flier, A., Liu, Z., Tan, S., Chen, K., Drager, D., Liu, T., et al. (2015). FcRn Rescues Recombinant Factor VIII Fc Fusion Protein from a VWF Independent FVIII Clearance Pathway in Mouse Hepatocytes. PLoS ONE, 10(4), e0124930-23. http://doi.org/10.1371/journal.pone.0124930.
Vorobjev et al., (1999). Oligonucleotide Conjugated to Linear and Branched High Molecular Weight Polyethylene Glycol as Substrates for RNase H. Nucleosides Nucleotides 18:2745-2750.
Wakabayashi, H., & Fay, P. J. (2013). Molecular orientation of Factor VIIIa on the phospholipid membrane surface determined by fluorescence resonance energy transfer. The Biochemical Journal, 452(2), 293-301. http://doi.org/10.1042/BJ20130025.
Wakabayashi, H., Koszelak, M. E., Mastri, M., & Fay, P. J. (2001). Metal Ion-independent Association of Factor VIII Subunits and the Roles of Calcium and Copper Ions for Cofactor Activity and Inter-Subunit Affinity †. Biochemistry, 40(34), 10293-10300. http://doi.org/10.1021/bi010353q.
Yee et al., A von Willebrand Factor Fragment Containing the D'D3 Domains is Sufficient to Stabilize Coagulation Factor VIII in Mice. Blood First Edition Paper, prepublished online May 21, 2014; DOI 10.1182/blood-2013-11-540534.
Zhou, H.-X. (2006). Quantitative Relation between Intermolecular and Intramolecular Binding of Pro-Rich Peptides to SH3 Domains. Biophysical Journal, 91(9), 3170-3181. http://doi.org/10.1529/biophysj.106.090258.
International Search Report and Written Opinion issued for Application No. PCT/US2016/046264, dated Oct. 31, 2016.
International Preliminary Report on Patentability issued for Application No. PCT/US2016/046264, dated Feb. 22, 2018.
Kelly, J. "A comparison protein, click chemistry approach to extended half life FVIII", Haemophilia 20180501 Blackwell Publishing Ltd NLD, vol. 24 No. supplement 5, May 1, 2018. Abstract.
The Extended European Search Report issued for European Application No. 16835805.9, dated Mar. 14, 2019.
Search Report and written Opinion issued for Singapore Application No. 11201800856P, dated Apr. 15, 2019.

\* cited by examiner

Scheme for construction of long half life FVIII

Scheme for the construction of a long half life, high activity FVIIa

Structural formula of TCO-PEG₃-Maleimide

Structural formula of 6-Methyl-Tetrazine-PEG₄-Maleimide

METHODS AND COMPOSITIONS RELATED TO LONG HALF-LIFE COAGULATION COMPLEXES

CROSS REFERENCE TO RELATED APPLICATIONS

This application claims the benefit of priority to U.S. Provisional Application No. 62/203,973, filed Aug. 12, 2015, which is incorporated herein by reference in its entirety.

BACKGROUND

Blood coagulation is controlled by a very complicated series of checks and balances such that coagulation only is triggered in the event of a bleed (Smith, Travers, & Morrissey, 2015). Injury sets off activation of these enzymes, resulting in an amplifying cascade of reactions that seals the wound. Hemophilia results from a defect in a gene coding for one of these proteins such that the cascade is aborted prematurely and bleeding continues. The most common forms of hemophilia, hemophilia A, hemophilia B and von Willebrand's disease, have long been treated by infusion of purified factor concentrates, replacing the defective enzyme and restoring the ability of the blood to clot.

Infusion of factor is remarkably effective, allowing afflicted individuals who may have died in childhood to have normal life expectancies (Hoots, 2003). With the increasing use of prophylaxis, that is, regularly scheduled infusions of factor to maintain a reasonable level of protection, these patients can lead essentially normal lives (Srivastava et al., 2012). This does not come without cost, literally and figuratively. Patients with severe hemophilia A need to infuse factor every other day due to the short circulatory half life of Factor VIII (FVIII), the protein missing in that form of the disease. This creates a number of problems, such as continued venous access and noncompliance.

Another very serious problem is encountered when patients develop inhibitory antibodies to the infused FVIII (Kempton & Meeks, 2014). About 30% of all hemophilia A patients will develop antibodies at some point in their therapy but about 5% develop such a serious inhibitor problem that FVIII infusion is no longer effective. This necessitates the use of "bypass" therapy. Factor VIIa (FVIIa) is one of the initiators of the coagulation cascade and can be used to step around the need for either FVIII or Factor IX (FIX) in the process. This requires very high concentrations of FVIIa and very frequent dosing since FVIIa has a circulatory half life of only two hours.

Because of these and other reasons, longer half-life factors are very desirable (Pipe, 2010). Less frequent dosing should improve compliance, venous access problems and expose the patient to a smaller mass of purified protein, perhaps reducing inhibitor formation. Moreover, longer half life proteins could expand treatment to the estimated 70% of hemophilia patients worldwide who are still untreated. Cost of factor is major issue but so is the complicated medical service required for hemophilia patients, particularly children. Since factor needs to be infused intravenously, rather than simply being injected subcutaneously, children with severe disease are most frequently treated at specialized hemophilia treatment centers. An obvious impediment to their treatment is that they must be delivered to the center several times per week which, in less developed countries, can put therapy beyond reach. Factors that persisted for longer periods of time could reduce these trips to once per week or even twice per month.

This problem has been recognized for some time and there have been numerous attempts to prolong the half life of factors. There are two common strategies for increasing the half life of therapeutic proteins. The first is to modify the proteins with chains of polyethylene glycol, commonly called PEGylation (Ginn, Khalili, Lever, & Brocchini, 2014). The PEG chains increase the water of hydration around the protein which results in reduced affinity for certain receptors and antibodies. The second strategy is to make use of the neonatal Fc receptor (FcRN) via fusion of the target protein with either the Fc portion of the immunoglobulins or human serum albumin (Andersen et al., 2011). Both immunoglobulins and albumin have long circulatory half lives due to their interaction with and protection by FcRN. When albumin or immunoglobulins are internalized in a variety of cells, they bind to FcRN and are recycled to the surface rather than being degraded. Both of these proteins have half lives of several weeks as a result.

These strategies have been successfully utilized to increase the half life of human Factor IX, the protein involved in hemophilia B (Mannucci & Mancuso, 2014). They have been less successful in prolonging the half life of FVIII (Buyue et al., 2014; Stennicke et al., 2013). FVIII itself is an unstable protein and requires the presence of von Willebrand Factor (vWF). FVIII in the absence of vWF has a half life of only a few minutes. The half life of the complex is determined by the half life of vWF so modifications to FVIII have only a small effect, increasing half-life from 12 hours to 18 hours.

Similar strategies have been attempted for FVIIa including PEGylation, fusion to albumin and Fc (Oldenburg & Albert, 2014; Schulte, 2008; van der Flier et al., 2015). Each of these modifications increased the half-life from 2 hours to over 10 hours but failed to solve another issue with FVIIa. FVIIa is most active in complex with Tissue Factor (TF). In the absence of TF, very high concentrations of FVIIa are needed to effect hemostasis. In some cases of engineered FVIIa, this has resulted in inhibitor formation.

Accordingly, there is a need for compositions and methods for long half-life coagulation complexes.

SUMMARY

Disclosed herein is a coagulation factor complex comprising: a coagulation factor; a fusion protein comprising a first protein fused to albumin, or an albumin fragment; and a modifying molecule, wherein the modifying molecule is coupled to the coagulation factor in such a way as to allow binding by the fusion protein, thereby creating a modified coagulation factor; wherein the modified coagulation factor and the fusion protein interact in at least two independent sites.

Disclosed are kits comprising the coagulation factor complexes disclosed herein.

Also disclosed are methods of treating a subject with a disease requiring coagulation factor infusion, the method comprising administering to the subject the coagulation factor complex disclosed herein. The disease can be hemophilia, for example. The administration of the coagulation factor complex to the subject result can result in a blood level half-life of the coagulation factor complex which is greater than the blood level half-life obtained upon administration of the coagulation factor alone. The coagulation factor complex can be administered to the subject via injection, inhalation, internasally, or orally.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A shows FVIII modified with either maleimide-PEG1000-laurate or maleimide-PEG1000-fluorescein isothiocyanate exhibit the same activity as the unmodified FVIII.

FIG. 4A shows a silver stained SDS polyacrylamide gel (4 to 20%) with untreated FVIII (Control) and modified FVIII (Modified FVIII). The modifying molecule is maleimide-PEG1000-biotin.

FIG. 5A shows FVIII chromatographed on Superdex 5200 Increase in 20 mM HEPES, pH 7.4, 150 mM NaCl, 4 mM $CaCl_2$, 0.01% Tween 20 and assayed for FVIII activity. FIG. 5B shows modified FVIII (maleimide-PEG1000-laurate) preincubated with 10 µg/ml human serum albumin before chromatography in the same buffer. Albumin shifts the molecular weight higher. FIG. 5C shows albumin does not affect the activity of modified FVIII.

FIG. 6A shows the structure and SDS acrylamide gel electrophoresis of the fusion protein monomer, CM110. FIG. 6B shows the structure and SDS acrylamide gel electrophoresis of the fusion protein dimer, CM210. FIG. 6C shows modified FVIII (modified with either maleimide-PEG1000-laurate or maleimide-PEG1000-myristate) preincubated with 10 µg/ml of the fusion protein monomer (CM110) before chromatography on Superdex 5200 Increase in 20 mM HEPES, pH 7.4, 150 mM NaCl, 4 mM $CaCl_2$, 0.01% Tween 20. FIG. 6D shows that the addition of CM110 has no effect on the activity of modified FVIII.

FIG. 7A shows the structure of the click chemistry reagents used to modify FVIII. FIG. 7B shows maleimide-PEG4-6 methyl tetrazine (MPT) does not affect the activity of FVIII. FIG. 7C shows incubation of MPT modified FVIII with the fusion protein CM110 modified with maleimide-PEG3-trans cyclooctene, results in a high molecular weight complex that retains FVIII activity after chromatography on Superdex 5200 Increase in 20 mM HEPES, pH 7.4, 150 mM NaCl, 4 mM $CaCl_2$, 0.01% Tween 20. FIG. 7D shows formation of the complex does not affect FVIII activity.

DETAILED DESCRIPTION

Figure 1:
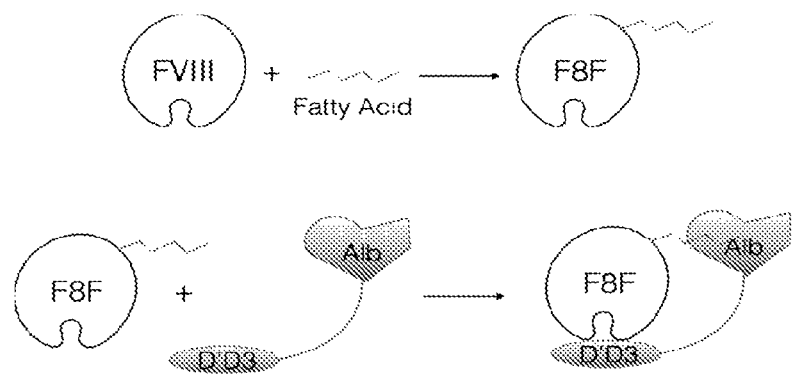
FIG. 1 shows a scheme for the construction of a long half-life coagulation factor VIII (coagulation factor complex, including a modified coagulation factor).
Figure 2:
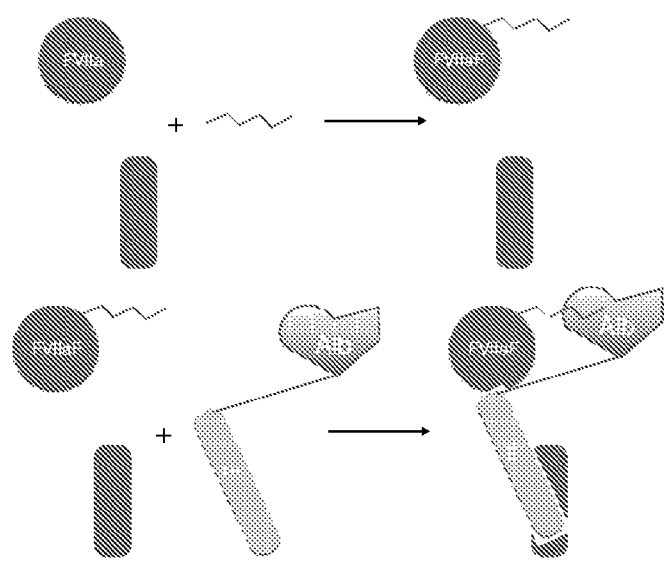
FIG. 2 shows the schematic for construction of a long half-life, high activity coagulation factor VIIa (coagulation factor complex, including a modified coagulation factor).

The materials, compositions, and methods described herein can be understood more readily by reference to the following detailed descriptions of specific aspects of the disclosed subject matter and the Examples and Figure included herein.

Before the present materials, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "an enzyme" includes mixtures of two or more such enzymes, reference to "the probiotic" includes mixtures of two or more such probiotics, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. "About" can mean within 5% of the stated value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "5" is disclosed, then "about 5" is also disclosed.

Disclosed herein are fragments or variants of polypeptides, and any combination thereof. The term "fragment" or "variant" when referring to polypeptide binding domains or binding molecules of the present invention include any polypeptides which retain at least some of the properties (e.g., coagulation activity for an FVIII variant or fragment, or FVIII binding activity for the vWF fragment, or recycling activity by an albumin fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

"Von Willebrand Factor," also referred to herein as "vWF," is a blood glycoprotein involved in hemostasis. The basic vWF monomer is a 2050-amino acid protein. Every monomer contains a number of specific domains with a specific function, including the D'D3 domain, which binds to factor VIII (Von Willebrand factor type D domain).

The term "endogenous vWF" as used herein indicates vWF molecules naturally present in plasma. The endogenous vWF molecule can be multimer, but can also be a monomer or a dimer. Endogenous vWF in plasma binds to FVIII and forms a non-covalent complex with FVIII.

The term "albumin fragment" as used herein means any albumin fragment or variant of full-length albumin that retains the ability to prolong the half-life of the fusion protein, as described herein. Such albumin fragments and variants are known to those of skill in the art. For example, Otagiri et al (2009), Biol. Pharm, Bull. 32(4), 527-534, discloses that 77 albumin variants are known, of these 25 have mutations in domain III. A natural variant lacking the C-terminal 175 amino acids at the carboxy terminus has been shown to have a reduced half-life (Andersen et al (2010), Clinical Biochemistry 43, 367-372). Iwao et al (2007) studied the half-life of naturally occurring human albumin variants using a mouse model, and found that K541 E and K560E had reduced half-life, E501 K and E570K had increased half-life and K573E had almost no effect on half-life (Iwao, et al (2007) B.B.A. Proteins and Proteomics 1774, 1582-1590). Galliano et al (1993) Biochim Biophys. Acta 1225, 27-32 discloses a natural variant E505K. Minchiotti et al (1990) discloses a natural variant K536E. Minchiotti et al (1987) Biochim Biophys. Acta 916, 41 1-418 discloses a natural variant K574N. Takahashi et al (1987) Proc. Natl. Acad. Sci. USA 84, 4413-4417, discloses a natural variant D550G. Carlson et a/(1992). Proc. Nat. Acad. Sci. USA 89, 8225-8229, discloses a natural variant D550A. These are all incorporated by reference in their entirety for their teachings concerning albumin fragments and variants.

The term "vWF fragment" or "vWF fragments" used herein means any vWF fragments that interact with FVIII and retain at least one or more properties that are normally provided to FVIII by full-length vWF, e.g., preventing premature activation to FVIIIa, preventing premature proteolysis, preventing association with phospholipid membranes that could lead to premature clearance, preventing binding to FVIII clearance receptors that can bind naked FVIII but not vWF-bound FVIII, and/or stabilizing the FVIII heavy chain and light chain interactions. The term "vWF fragment" as used herein does not include full length- or mature vWF protein. In a particular embodiment, the "vWF fragment" as used herein comprises a D' domain and a D3 domain of the VWF protein, but does not include the A1 domain, the A2 domain, the A3 domain, the D4 domain, the B1 domain, the B2 domain, the B3 domain, the CI domain, the C2 domain, and the CK domain of the vWF protein. vWF fragments and variants are known to those of skill in the art and are disclosed herein.

A "fusion" or "chimeric" protein comprises a first amino acid sequence linked to a second amino acid sequence with which it is not naturally linked in nature. In one embodiment, the term "fusion protein," as used herein, in one example refers to the fusion of the von Willebrand's factor fragment, e.g. D'D3 to albumin, or an albumin fragment. Also disclosed is albumin linked to Tissue Factor (TF) for Factor VIIa.

Disclosed herein is a "modifying molecule." A modifying molecule is any molecule capable of modifying a coagulation factor so that it may interact with a fusion protein while retaining the coagulation enhancing activity of the coagulation factor, e.g. factor VIII (FVIII). For example, a FVIII can be modified with a polyethylene glycol chain and capped by a fatty acid. Various examples of modifying molecules are discussed herein.

A "modified coagulation factor" refers to a coagulation factor which has been modified by a modifying molecule so that it is capable of interacting with a fusion protein while retaining sufficient coagulation activity. The modified coagulation factor can also be referred to as a derivatized FVIII or F8F herein. The modified coagulation factor can, for example, be bound to a fusion protein of D'D3 attached by an appropriate sized linker to human albumin in such a way that albumin can bind the fatty acid attached to the modified FVIII to form the modified coagulation factor complex, for example the Factor VIII or Factor VIIa complex of the subject invention.

As used herein, the term "half-life" refers to a biological half-life of a particular polypeptide in vivo. Half-life may be represented by the time required for half the quantity administered to a subject to be cleared from the circulation and/or other tissues in the animal.

The term "half-life limiting factor" or "FVIII half-life limiting factor" as used herein indicates a factor that prevents the half-life of a FVIII protein from being longer than 1.5 fold or 2 fold compared to wild-type FVIII. For example, full length or mature vWF can act as a FVIII half-life limiting factor by inducing the FVIII and vWF complex to be cleared from the system by one or more vWF clearance pathways. In one example, endogenous vWF is a FVIII half-life limiting factor. In another example, a full-length recombinant vWF molecule non-covalently bound to a FVIII protein can be a FVIII-half-life limiting factor.

The terms "interacts with" or "linked to" as used herein refers in one embodiment to a covalent or non-covalent linkage. The term "covalently linked" or "covalent linkage" refers, for example, to a covalent bond, e.g., a disulfide bond, a peptide bond, or one or more amino acids. In another embodiment "interacts with" or "linked to" means the proteins or protein fragments disclosed herein are connected by a linker between the two proteins or protein fragments that are linked together, for example, between the FVIII and the albumin, and/or between the D'D3 and albumin. The first amino acid can be directly joined or juxtaposed to the second amino acid or alternatively an intervening sequence can covalently join the first sequence to the second sequence. The term "linked" can mean not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be joined to a second amino acid sequence by a peptide bond or a linker. The linker can be a peptide or a polypeptide or any chemical moiety, for example click chemistry.

The coagulation factor complexes disclosed herein can be used prophylactically. As used herein the term "prophylactic treatment" refers to the administration of a molecule prior to a bleeding episode or consistently during normal activity to prevent a bleeding episode. In one embodiment, the subject in need of a general hemostatic agent is undergoing, or is about to undergo, surgery. The coagulation factor complex can be administered prior to or after surgery as a prophylactic. The coagulation factor complex can be administered during or after surgery to control an acute bleeding episode. The surgery can include, but is not limited to, liver transplantation, liver resection, dental procedures, or stem cell transplantation.

The coagulation factor complexes of the invention can also be used for on-demand (also referred to as "episodic") treatment. The term "on-demand treatment" or "episodic treatment" refers to the administration of a chimeric molecule in response to symptoms of a bleeding episode or before an activity that may cause bleeding. In one aspect, the on-demand (episodic) treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject may have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition.

In one embodiment, the term "treating" or "treatment" means maintaining a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering a coagulation factor complex of the invention. In another embodiment, treating or treatment means maintaining a FVIII trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FVIII activity in a non-hemophiliac subject. The minimum trough level required for treatment can be measured by one or more known methods and can be adjusted (increased or decreased) for each person.

Coagulation Factor Complexes

Human albumin has a series of properties that are useful in the construction of fusion proteins described herein. It has the ability to prolong the half life of fusion proteins by binding to the neonatal Fc receptor and it binds a number of small molecules including fatty acids and bilirubin. In addition, it has a single exposed sulfhydryl group that can be utilized to attach various ligands. As utilized herein these properties allow the construction of a long half life FVIII, as well as a long half life, high activity version of FVIIa. The coagulation factor complexes disclosed herein comprise: a coagulation factor; a fusion protein comprising a first protein fused to albumin, or an albumin fragment; and a modifying molecule, wherein the modifying molecule is coupled to the coagulation factor in such a way as to allow binding by the fusion protein, thereby creating a modified coagulation factor; wherein the modified coagulation factor and the fusion protein interact in at least two independent sites. The modifying molecule can also be coupled to the fusion protein in such a way as to allow binding of the fusion protein to the coagulation factor or to cause a chemical reaction between the coagulation factor and the fusion protein. The combination of the coagulation factor with the modifying molecule can be referred to a modified coagulation factor, e.g., modified Factor VIII and VIIa, herein. The modified coagulation factor and the fusion protein interact in at least two independent sites. The coagulation factor can be a Factor VIIa, for example. In another embodiment, the coagulation factor can be Factor VIII.

Coagulation Factor vWF is a very large molecule and circulates as a large multimeric complex of these large molecules (Lenting, Christophe, & Denis, 2015). It is so large that it is ingested into macrophages and digested as a particle. Attempts to engineer a smaller fragment of vWF, called D'D3, that protects FVIII have been successful and fusing this fragment to the Fc region increases its half life dramatically (Yee et al., 2014). In vWF deficient mice, this D'D3-Fc fusion increases the half life of FVIII from about 15 hours to over 7 days.

The binding constant for vWF and FVIII is about 0.3 nM (Orlova, Kovnir, Vorobiev, Gabibov, & Vorobiev, 2013). The measured binding constant of the D'D3-Fc fusion created by Yee, et al. (Yee et al., 2014) is 1.5 nM. FVIII binds tightly but reversibly to vWF such that there is always about 1 to 2 percent of the FVIII free in solution. In both mice and humans, vWF exists at about a fifty-fold higher concentration than FVIII. Between the lower binding constant and the much higher concentration of vWF, FVIII can be quickly competed away from the D'D3-Fc fusion.

One potential solution to these problems is found by fusing D'D3 to albumin, thereby creating a "fusion protein," as it is referred to herein. Albumin is the most abundant protein in the blood (Peters, 1995). Its 19 day half life in the circulation is determined by its ability to bind to the FcRN, as described earlier. It serves two major roles: one is to maintain the osmolarity of the blood and the second is to transport hydrophobic molecules. Albumin is the major transporter of fatty acids. A strategy that has been employed successfully to increase the half life of insulin, for example, is to conjugate insulin to myristic acid, a 14 carbon fatty acid. This molecule is called insulin detemir (Philips & Scheen, 2006). When injected, the fatty acid quickly binds to albumin, increasing the half life of the insulin from 4 minutes to 5 hours.

A combination of these two ideas is disclosed herein (FIG. 1) in a novel molecule to solve the long existing half life problem and provide a much needed solution. For example, first, the FVIII can be modified with a polyethylene glycol chain and capped by a fatty acid, for example. This example of a "modifying molecule," as it is referred to herein, creates an example of a "modified coagulation factor." The fatty acid thus protrudes from the FVIII molecule in one embodiment to create the modified coagulation factor. The modified coagulation factor can also be referred to as a derivatized FVIII or F8F herein. Next, the modified coagulation factor can be bound to a fusion protein of D'D3, derived from vWF, attached by an appropriate sized linker to human albumin, in such a way that albumin can bind the fatty acid attached to the modified FVIII to form the modified coagulation factor complex, for example the Factor VIII or Factor VIIa complex of the subject invention. The D'D3 fragment can bind to its cognate site on the modified FVIII and the fatty acid can bind to albumin. The modified coagulation factor can be tethered to the fusion protein at two points, both of which have strong binding constants. In addition, the length of the linker connecting D'D3 to albumin in the fusion protein can be altered, either longer or shorter, such that D'D3, can be properly or optimally orientated with the Factor VIII binding site for optimal half life extension. In this way, it is much less likely that native vWF will be able to compete effectively for the modified FVIII and attachment to albumin increases the half life substantially.

The modified coagulation factor and the fusion protein can interact at one, two, three, four, or more sites. In one embodiment, the modified coagulation factor and the fusion protein interact at two independent sites on both molecules. By "independent sites" is meant non-overlapping, or distinct, areas of one, or both, molecules. At least one binding site of the modified coagulation factor can be a natural binding site. In other words, the binding site is naturally occurring on the coagulation factor, and is not part of its modification. The other binding site on the modified coagulation factor can be modified, such that one or more amino acids in that site is not natural, or native, to the coagulation factor.

The fusion protein can comprise two, three, four, or more proteins fused together. For example, the first fusion protein can comprise a D'D3 fragment of von Willebrand's factor. Variants and fragments of vWF are known to those of skill in the art, and are contemplated herein. Examples of such can be found in U.S. Pat. No. 9,125,890, and U.S. Patent Applications 2014/0357564 and 2013/120939. Alternatively, the first fusion protein can comprise Tissue Factor (TF). The second protein can comprise albumin, or an immunoglobulin Fc fragment. In one example, the immunoglobulin Fc fragment can comprise a single chain variable region (scFv) specific to the modified coagulation factor. The scFv can be specific to a modified site of the modified coagulation factor.

Figure 5A:
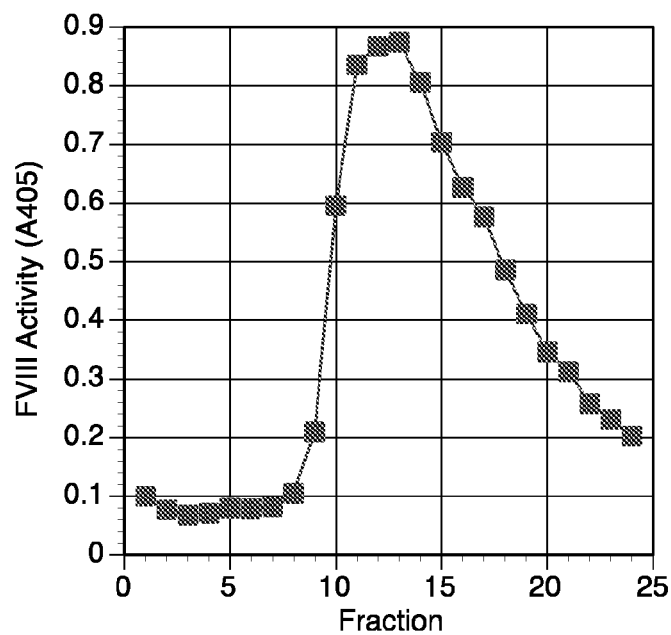
FIGS. 5A-C show albumin binds to the modified FVIII.
Figure 5B:
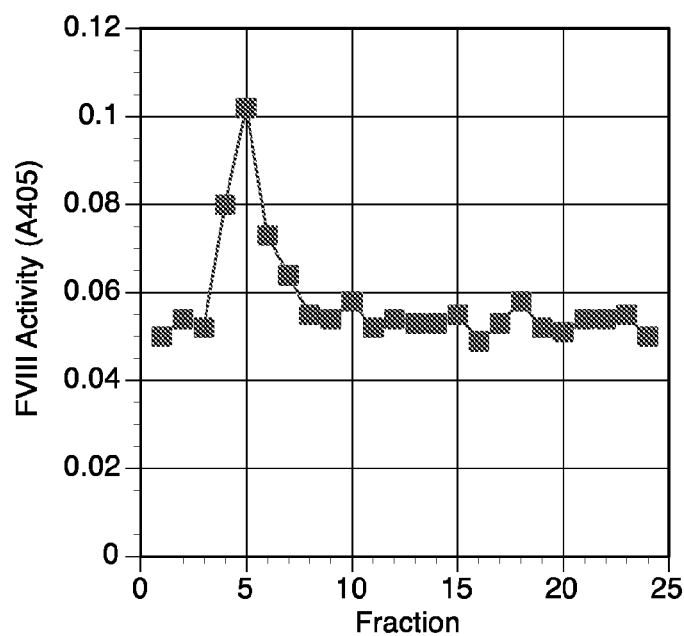
Figure 5C:
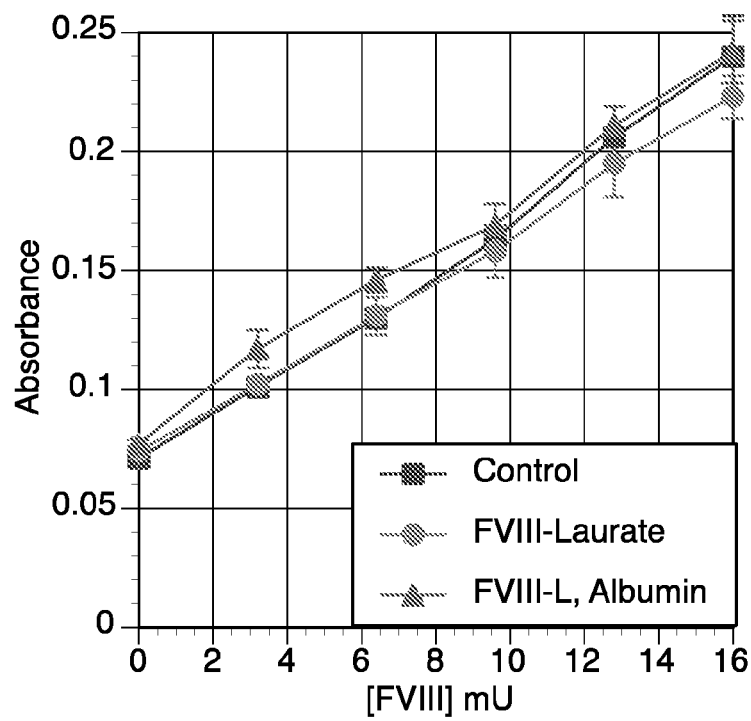

FIG. 5 demonstrates that albumin can bind to the modified FVIII and that it again has no effect on FVIII activity. Panel A shows chromatography of FVIII modified with maleimide-PEG1000-laurate on a Superdex 200 size exclusion column, assayed by FVIII activity. Panel B shows that the addition of albumin to the derivatized FVIII shifts the molecular weight higher, as expected. Panel C demonstrates that albumin bound to derivatized FVIII does not compromise FVIII activity.

Figures 6A, 6B:
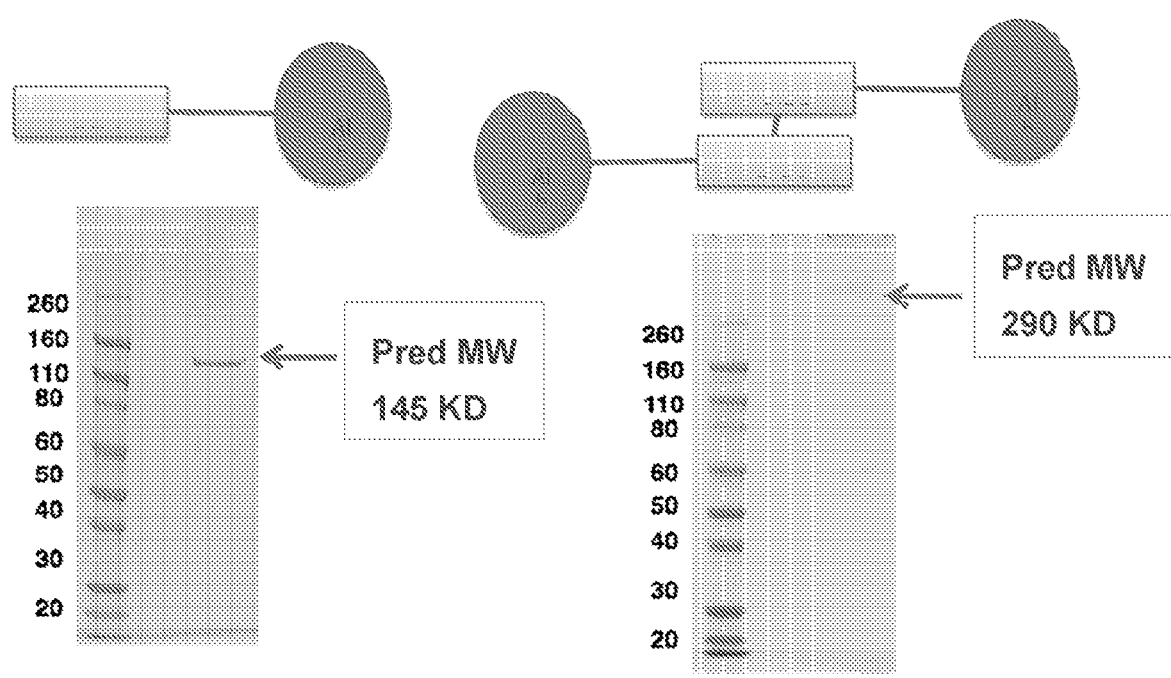
FIGS. 6A-D show the structure of the fusion proteins and formation of the modified factor complex.
Figure 6C:
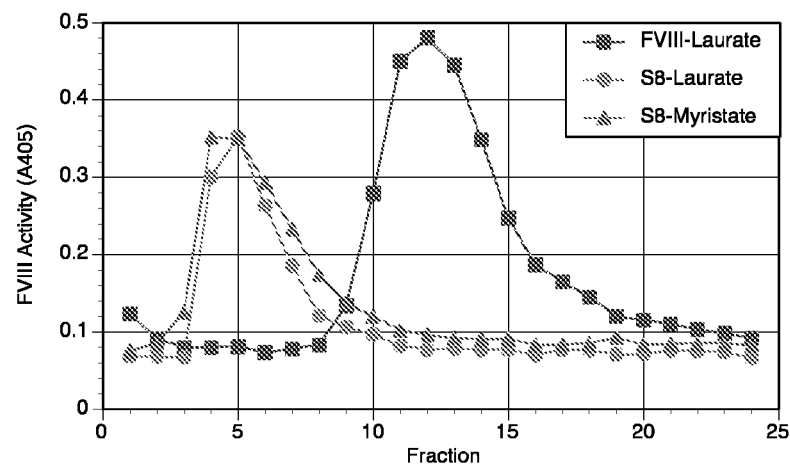
Figure 6D:
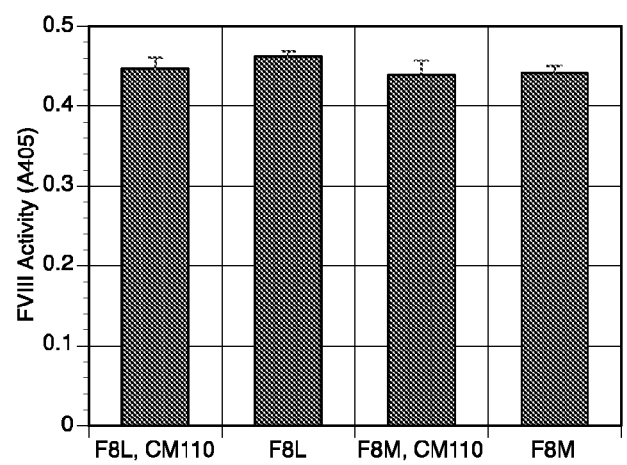
Figure 7A:
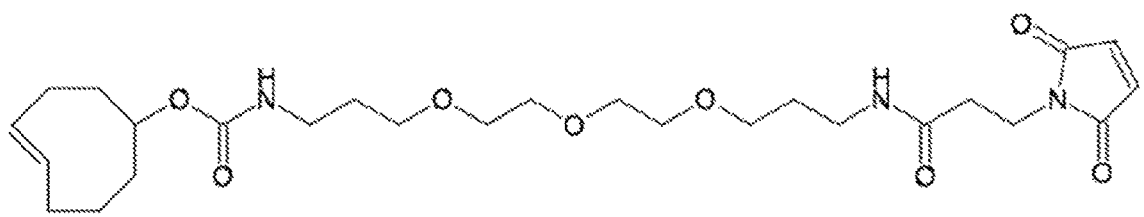
FIGS. 7A-D show click chemistry to ligate modified FVIII to the fusion protein.
Figure 7A:
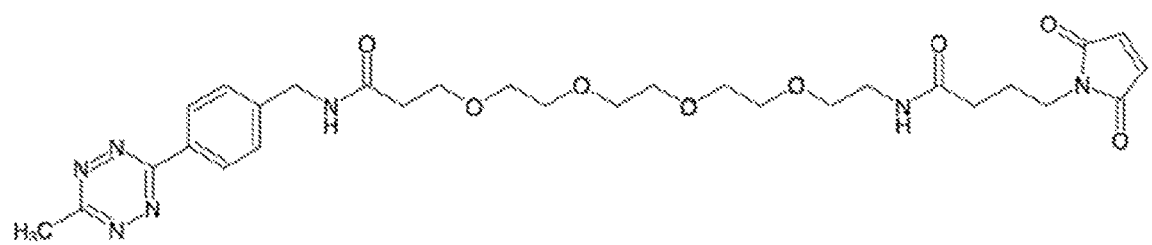
Figure 7B:
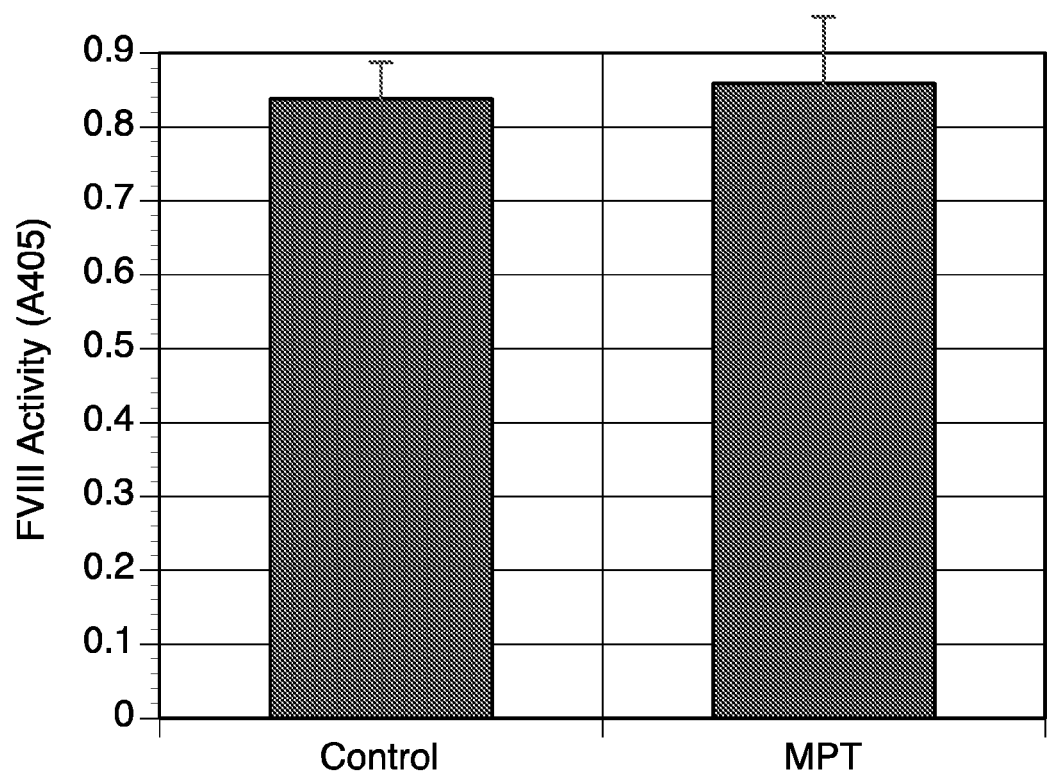
Figure 7C:
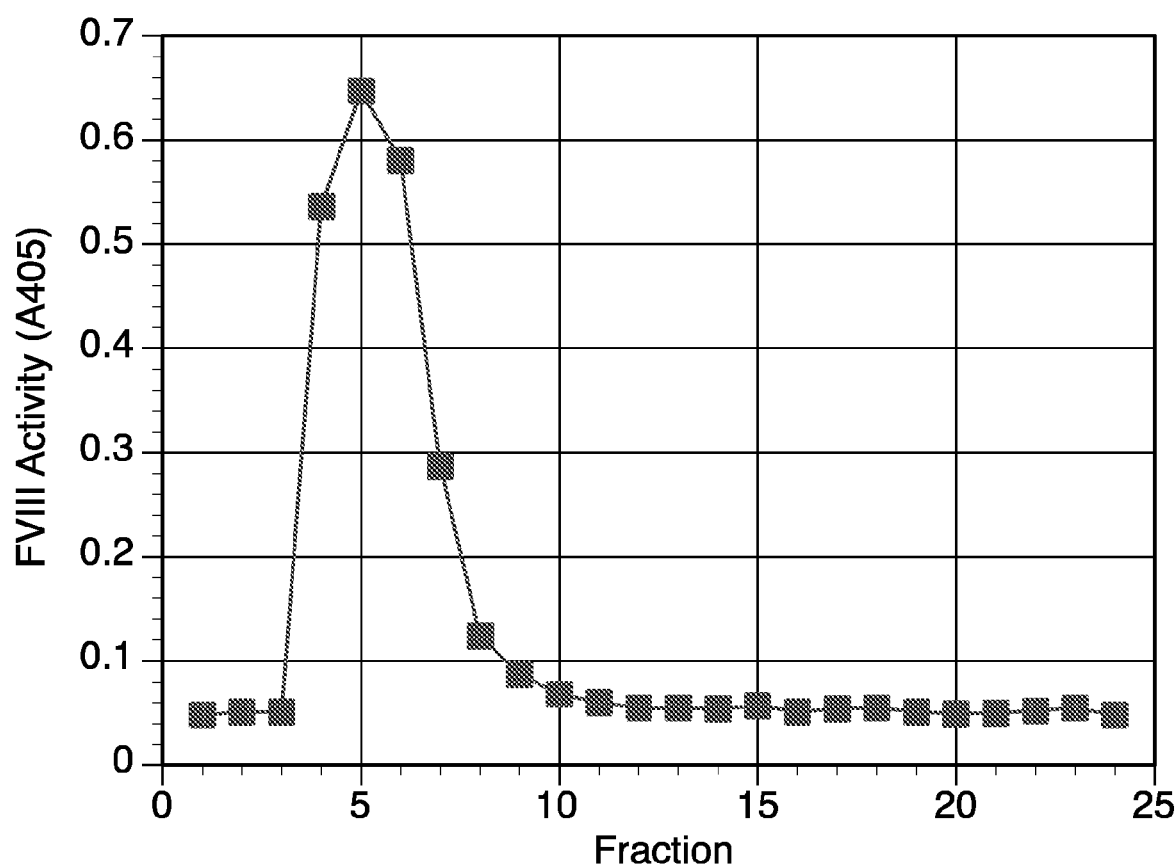
Figure 7D:
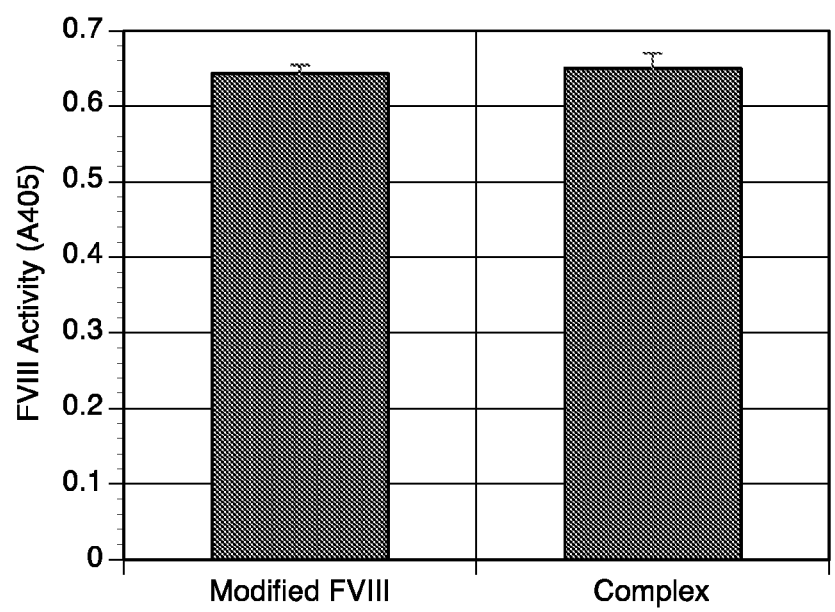

Two versions of the fusion protein have been produced by transfection into C3A cells (ATCC CRL-10741), a human liver cell line. CM110 in FIG. 6, panel A, consists of the D'D3 fragment of von Willebrand Factor, a 56 amino acid glycine, serine rich linker and a full length human albumin CM210 (FIG. 6, panel B) is a dimer of this molecule, joined by sulfhydryl links through the D'D3 region. When FVIII modified with either maleimide-PEG1000-laurate or maleimide-PEG1000-myristate is incubated with CM110, they spontaneously form the modified coagulation factor complex that shifts the activity of the FVIII to a higher molecular weight, as shown in FIG. 6, Panel C. While CM110 was in excess in this experiment, it is important to note that all of the FVIII activity is shifted to the higher molecular weight. Neither CM110 nor CM210 affect activity of modified FVIII (FIG. 6, Panel D).

This dual binding strategy can be accomplished in a number of other ways while still maintaining the required FcRN cycling, as those of skill in the art will appreciate in view of this disclosure. Other ligands can replace the fatty acid in the modifying molecule, since albumin is known to bind a wide variety of ligands, such as bilirubin (Peters, 1995).

Another embodiment is to substitute an antibody/small molecule set for the albumin/fatty acid pair. There are many small molecules that have cognate monoclonal antibodies and these are often used for detection of the small molecule in biological specimens (Bradbury, Sidhu, Dübel, & McCafferty, 2011). A molecule can be constructed that has D'D3, an amino acid spacer, the Fc region of the immunoglobulins and a single chain variable region, specific for a small molecule, for example, nitrotyrosine. The modifying molecule could then take the form of maleimide-PEG1000-nitrotyrosine.

Another alternative using a similar strategy of modifying FVIII can be used to create a covalent link between the coagulation factor and the fusion protein. Click chemistry or bio-orthogonal chemistry describes molecules that are designed to react only with one another in a complex chemical milieu. Panel A in FIG. 7 shows two such molecules of the general structure maleimide-$PEG_N$-X where in this case X is methyl tetrazine on one and trans cyclooctene (TCO) on the other. As before, modifying FVIII with the methyl tetrazine containing molecule has no effect on activity (Panel B, FIG. 7). The only free sulfhydryls on CM110 and CM210, the fusion proteins described herein, are those corresponding to cysteine 34 in albumin By modifying CM110 or CM210 with maleimide-PEG3-TCO and FVIII with maleimide-PEG4-methyltetrazine, then mixing, a covalently linked complex forms when TCO reacts with methyltetrazine. Panel C shows that addition of maleimide-PEG3-TCO modified CM110 to maleimide-PEG4-methyl tetrazine modified FVIII results in a high molecular weight complex that still retains the FVIII activity. Panel D again demonstrates that formation of the covalent complex does not affect activity.

The mathematics of intramolecular binding has been described by Kramer and Karpen (Kramer & Karpen, 1998) and in more detail by Zhou (Zhou, 2006). Binding becomes a function of the individual dissociation constants and the effective local concentration. The bond between albumin in the fusion protein and the modified FVIII, for example, tethers the D'D3 fragment to the modified FVIII. The local concentration of the D'D3 fragment then becomes quite high, precluding binding of endogenous vWF. Since the dissociation constants for either D'D3 binding to FVIII or fatty acid binding to albumin are in the nanomolar range, binding of the fusion protein to modified FVIII should be tight. In the case of the click chemistry modified complex, the link is covalent.

This dual binding strategy overcomes at least two problems encountered by Yee, et al. [2](Yee et al., 2014). The first is to increase the binding affinity of FVIII for the fusion protein and prevent dilution by the existing high concentration of vWF in the serum. Binding should now be a product of both binding constants and the effective concentration so neither free vWF nor free fatty acids should be able to compete effectively for binding.

This molecule, referred to herein as the modified coagulation factor complex, has several desirable features not afforded by either FVIII or other long half life FVIII molecules. First, the very tight or covalent binding ensures that there is very little dissociation of the modified FVIII from the fusion protein, preventing loss of the administered FVIII into the large pool of normal vWF. Second, by divorcing the modified coagulation factor complex from the endogenous vWF and using the fusion protein to extend the half life, it should obtain a half-life similar to that shown by Yee, et al. (Yee et al., 2014) for their D'D3-Fc protein, which was over seven days. Third, by administering the modified coagulation complex rather than free FVIII, it can reduce the incidence of inhibitor formation. Fourth, by attaching the albumin to the fusion protein, rather than directly to the FVIII, the FVIII activity is preserved. Direct fusion of albumin to FVIII results in an inactive molecule{Powell:2015gu}. Positioning albumin away from direct contact with the FVIII should assist efficient recycling by the FcRN. Finally, this is an entirely human protein produced in a human cell system, which can further reduce the incidence of inhibitor formation.

The half-life of the coagulation factor complex comprising the modified coagulation factor VIII can be at least 10, 20, 30, 40, 50, 60, 70, 80, 90, or 100% or greater compared to a coagulation factor alone. The coagulation factor complex can also have a half-life that is 2, 3, 4, 5, 6, 7, 8, 9, or 10 or more times longer, when compared to an unmodified coagulation factor. More specifically, the half-life of the coagulation factor complex can be at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer or more than the half-life of a FVIII protein alone. In one embodiment, the half-life of FVIII is about 1.5-fold to about 20-fold, about 1.5 fold to about 15 fold, or about 1.5 fold to about 10 fold longer than the half-life of wild-type FVIII. In another embodiment, the half-life of the FVIII when in the coagulation factor complex is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to wild-type FVIII or a FVIII protein alone. In other embodiments, the half-life of the coagulation factor complex is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours. In still other embodiments, the half-life of the coagulation factor complex is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life of the coagulation factor complex per subject is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

Long Half Life, High Activity FVIIa

Figure 3A:
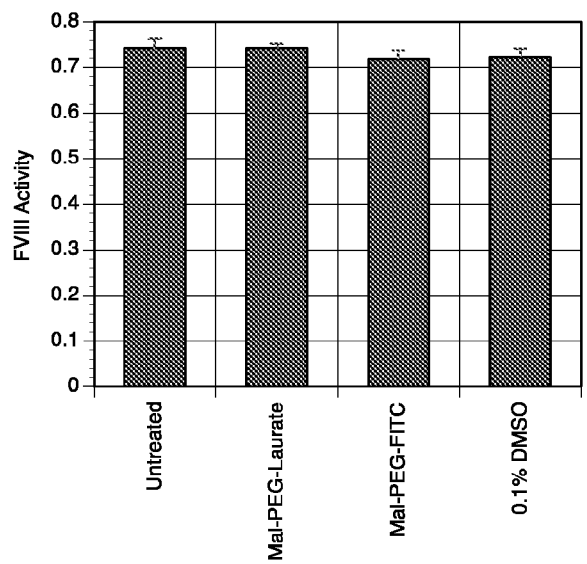
FIGS. 3A and B show that the attachment of a modifying molecule to FVIII does not interfere with its activity.
Figure 3B:
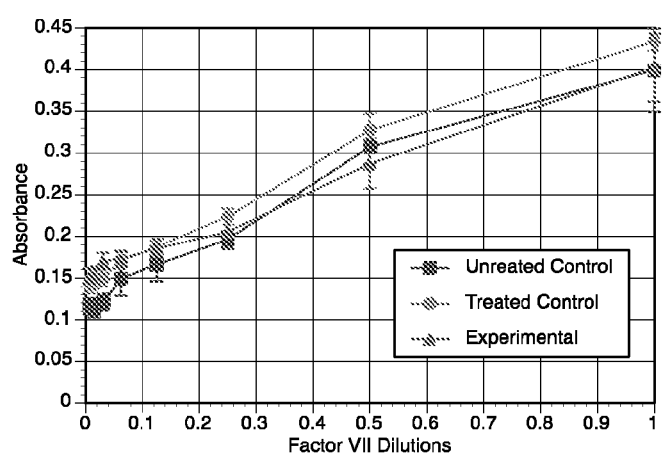
FIG. 3B shows untreated FVIII, FVIII subjected to the same experimental conditions but without the modifying molecule and FVIII treated with the modifying molecule, maleimide-PEG1000-laurate, have the same activity.
Figure 4A:
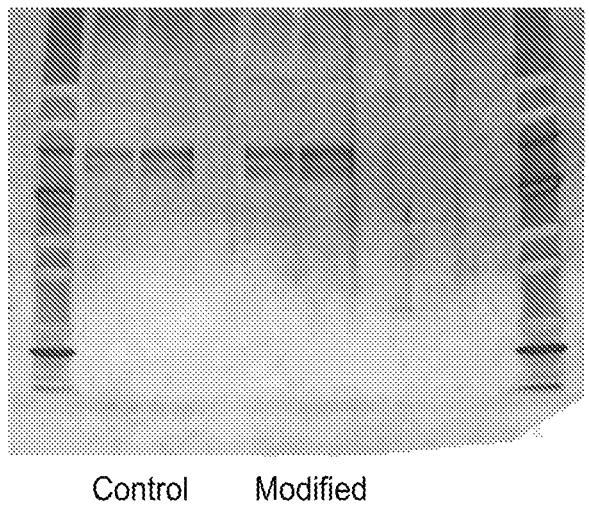
FIGS. 4A and B show the modifying molecule attaches to the heavy chain of FVIII.
Figure 4B:
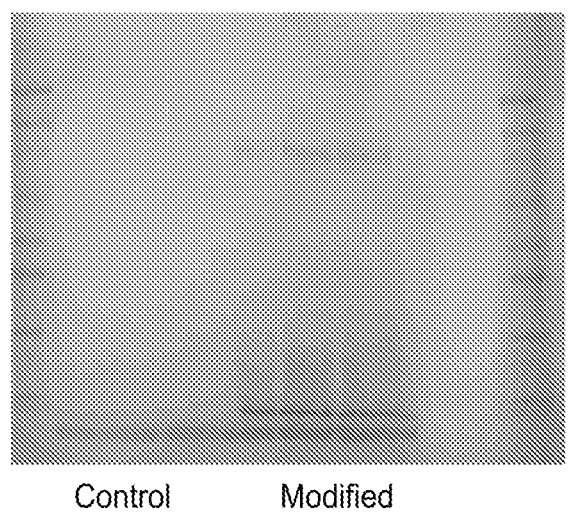
FIG. 4B shows an electroblot of a similar gel. The blot was probed with an avidin-horse radish peroxidase (HRP) then stained for HRP to visualize the modifying molecule.

A similar strategy can be applied to creating a long half-life, high activity FVIIa (FIG. 3). Under normal coagulation conditions, FVII is first activated by proteolysis to FVIIa. FVIIa, however has very low activity for carrying out its function, which to activate Factor X (FX). When FVIIa encounters membrane bound Tissue Factor at the site of injury, it binds to form a complex with over 100 fold higher activity in production of FXa (Vadivel & Bajaj, 2012). Ordinarily, FVIIa is present at very low concentrations and only serves to set off the amplifying cascade of blood coagulation. As a bypass agent, FVIIa is administered at very high concentrations such that it can activate sufficient FX to FXa to provide the thrombin burst required to form a fibrin clot.

Similar to the long half life FVIII example disclosed above, TF has a dissociation constant for FVIIa of about 1 nM (Vadivel & Bajaj, 2012). By first derivatizing FVIIa with a water soluble fatty acid, then binding it to a soluble Tissue Factor—albumin fusion protein, a complex with several desirable properties should be created. The complex can have 2, 10, 20, 30, 40, 50, 60, 70, 80, 90, or 100 or more fold increased activity with respect to activation of FX. This allows effective bypass therapy with substantially less protein than is currently used, reducing both cost and the chance of immunogenicity. The half life of the complex can be increased by virtue of recycling via FcRN as a result of the albumin fusion, resulting in less frequent administration. This is an important consideration for FVIIa due to its very short 2 hour half-life. Even a modest extension is helpful, but this molecule can confer a particularly long half life. Binding of antithrombin III (ATIII) to FVIIa is one of the main routes of clearance of FVIIa activity (Lawson, Butenas, Ribarik, & Mann, 1993). ATIII is most effective in inactivating FVIIa in the presence of heparin and when TF is membrane bound. Studies of ATIII mediated inactivation of FVIIa have demonstrated that ATIII displaces FVIIa from TF and then prevents rebinding. The presence of a tightly attached TF should prevent binding of the derivatized FVIIaF to membrane bound TF and perhaps prevent ATIII inactivation.

Modifying Molecules

"Modifying molecules," as disclosed herein, can comprise any molecule which modifies a coagulation factor and renders it capable of interacting with a fusion protein. The modifying molecule can, for example, comprise a fatty acid. The modifying molecule can be attached to the modified coagulation factor through a polyethylene glycol chain, for example. A first and a second protein of the fusion protein can be joined together via a linker, for example. The modified coagulation factor can comprise one or more modified amino acids. Additionally, or alternatively, the fusion protein can comprise modified amino acids. For example, coagulation factor complexes of the invention can, in some embodiments, be composed of amino acids joined to each other by peptide bonds or modified peptide bonds, i.e., peptide isosteres, and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature.

Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York; pgs. 1-12 (1983); Seifter et al., Meth. Enzymol. 182:626-646 (1990); Rattan et al., Ann. N.Y. Acad. Sci. 663:48-62 (1992)).

FVIII can be modified by a number of modifying molecules of the general structure maleimide-PEGn-X, shown in Table 1. A variety of such modifying molecules can be used. For example, various modifications of maleimide-PEG are known to those of skill in the art, such as those presented in U.S. Pat. No. 6,828,401, hereby incorporated by reference in its entirety for its disclosure concerning PEG-maleimide derivatives. In the examples of this invention, this modification did not have any observed effect on the activity of FVIII. FIG. 3 shows FVIII activity before and after modification with either Mal-PEG-laurate or Mal-PEG-FITC. FIG. 4 shows SDS containing polyacrylamide gels. Panel A is a silver stained gel showing that derivatization has no effect on the molecular weight or structure of FVIII. Panel B shows a protein blot of another gel that was then probed with streptavidin—HRP to visualize the modifying molecule, in this case, maleimide-PEG5000-biotin. The result shows that the Mal-PEG-biotin molecule reacts with the heavy chain of FVIII. Examples of modifying molecules can be found in Table 1.

TABLE 1

| Molecules used to modify FVIII |
|---|
| Maleimide-PEG5000-biotin |
| Maleimide-PEG1000-fluorescein isothiocyanate |
| Maleimide-PEG1000-laurate |
| Maleimide-PEG1000-myristate |
| Maleimide-PEG4-6-methyl tetrazine |
| Maleimide-PEG3-trans cyclooctene |

The chemical moieties for modification of the coagulation factor may be selected from water soluble polymers such as polyethylene glycol, ethylene glycol/propylene glycol copolymers, carboxymethylcellulose, dextran, polyvinyl alcohol and the like. The coagulation factors may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, such as, for example, the method disclosed in EP 0 401 384 (coupling PEG to G-CSF), herein incorporated by reference; see also Malik et al., Exp. Hematol. 20:1028-1035 (1992), reporting pegylation of GM-CSF using tresyl chloride. For example, polyethylene glycol may be covalently bound through amino acid residues via reactive group, such as a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the coagulation factors of the invention may be accomplished by any number of means. For example, polyethylene glycol may be attached to the molecule either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monomethoxy polyethylene glycol (MPEG) using tresylchloride. Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichlorophenylcarbonate, MPEG-p-nitrophenolcarbonate, and various MPEG-succinate derivatives. A number of additional polyethylene glycol derivatives and reaction chemistries for attaching polyethylene glycol to proteins are described in International Publication No. WO 98/32466, the entire disclosure of which is incorporated herein by reference. Pegylated protein products produced using the reaction chemistries set out herein are included within the scope of the invention.

The number of polyethylene glycol moieties attached to a modified coagulation factor of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., Crit. Rev. Thera. Drug Carrier Sys. 9:249-304 (1992).

The polypeptides of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

The presence and quantity of modified coagulation factor complexes of the invention may be determined using ELISA, a well known immunoassay known in the art. In one ELISA protocol that would be useful for detecting/quantifying modified molecules of the invention, comprises the steps of coating an ELISA plate with an anti-human serum albumin antibody, blocking the plate to prevent non-specific binding, washing the ELISA plate, adding a solution containing the molecule of the invention (at one or more different concentrations), adding a secondary anti-therapeutic protein specific antibody coupled to a detectable label (as described herein or otherwise known in the art), and detecting the presence of the secondary antibody. In an alternate version of this protocol, the ELISA plate might be coated with the anti-therapeutic protein specific antibody and the labeled secondary reagent might be the anti-human albumin superfamily specific antibody.

Polypeptide and Polynucleotide Fragments and Variants

The present invention is further directed to fragments of the coagulation factor complexes described herein as well as fragments of individual components of the coagulation factor complexes, such as the modified coagulation factor, the modifying molecule, or the fusion protein. These modifications can include those disclosed herein, which modify the molecules in such a way as to increase activity or half life, or other modifications that enhance the properties of the molecule or make it desirable for other reasons.

Even if a deletion of one or more amino acids results in modifications or loss of one or more functions, the coagulation function of the complex may still be retained. Accordingly, fragments of the molecules disclosed herein, include the full length protein as well as polypeptides having one or more residues deleted from the amino acid sequence of the reference polypeptide, are contemplated herein.

The present application is directed to proteins containing polypeptides at least 50%, 55%, 60%, 65%, 70%, 75%, 80%, 85%, 90%, 95%, 96%, 97%, 98% or 99% identical to a reference polypeptide sequence (e.g., a coagulation factor, a modifying molecule, or a fusion protein) set forth herein, or fragments thereof.

"Variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide.

As used herein, "variant" refers to a protein disclosed herein which differs in sequence from the known sequence of the protein, but retains at least one functional and/or therapeutic property thereof (e.g., a therapeutic activity and/or biological activity, including but not limited to coagulation) as described elsewhere herein or otherwise known in the art. Generally, variants are overall very similar, and, in many regions, identical to the amino acid sequence of the protein of interest or albumin superfamily protein.

The present invention is also directed to proteins which comprise, or alternatively consist of, an amino acid sequence which is at least 80%, 85%, 90%, 95%, 96%, 97%, 98%, 99% or 100%, identical to, for example, the amino acid sequence of the coagulation factor itself, the fusion protein, or the modifying molecule. Fragments of these polypeptides are also provided (e.g., those fragments described herein). Further polypeptides encompassed by the invention are polypeptides encoded by polynucleotides which hybridize to the complement of a nucleic acid molecule encoding an amino acid sequence of the invention under stringent hybridization conditions (e.g., hybridization to filter bound DNA in 6 times sodium chloride/sodium citrate (SSC) at about 45 degrees Celsius, followed by one or more washes in 0.2 times SSC, 0.1% SDS at about 50-65 degrees Celsius), under highly stringent conditions (e.g., hybridization to filter bound DNA in 6 times sodium chloride/sodium citrate (SSC) at about 45 degrees Celsius, followed by one or more washes in 0.1 times SSC, 0.2% SDS at about 68 degrees Celsius), or under other stringent hybridization conditions which are known to those of skill in the art (see, for example, Ausubel, F. M. et al., eds., 1989 Current protocol in Molecular Biology, Green publishing associates, Inc., and John Wiley & Sons Inc., New York, at pages 6.3.1-6.3.6 and 2.10.3). Polynucleotides encoding these polypeptides are also encompassed by the invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence of a coagulation factor or a fragment, can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are either both nucleotide sequences or both amino acid sequences. The result of said global sequence alignment is expressed as percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

The polynucleotide variants of the invention may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, polypeptide variants in which less than 50, less than 40, less than 30, less than 20, less than 10, or 5-50, 5-25, 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host, such as, yeast or E. coli).

Naturally occurring variants are called "allelic variants," and refer to one of several alternate forms of a gene occupying a given locus on a chromosome of an organism. (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the polypeptide of the present invention without substantial loss of biological function. As an example, Ron et al. (J. Biol. Chem. 268: 2984-2988 (1993)) reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988).)

Thus, the invention further includes polypeptide variants which have a functional activity (e.g., biological activity and/or therapeutic activity). In highly preferred embodiments the invention provides modifications to coagulation factors, which modifications allow for an increased functional activity, such as a prolonged half-life.

Also disclosed are methods of treating a subject with a disease requiring coagulation factor infusion, the method comprising administering to the subject the coagulation factor complex disclosed herein. The disease can be hemophilia, for example. The administration of the coagulation factor complex to the subject result can result in a blood level half-life of the coagulation factor complex which is greater than the blood level half-life obtained upon administration of the coagulation factor alone. The coagulation factor complex can be administered to the subject via injection, inhalation, internasally, or orally.

The modified coagulation factor complexes of the invention or formulations thereof may be administered by any conventional method including parenteral (e.g. subcutaneous or intramuscular) injection or intravenous infusion. The treatment may consist of a single dose or a plurality of doses over a period of time.

The coagulation factor complexes disclosed herein can be present as a pharmaceutical formulation, together with one or more acceptable carriers. The carrier(s) must be "acceptable" in the sense of being compatible with the coagulation factor complex, and not deleterious to the recipients thereof.

The formulations may conveniently be presented in unit dosage form and may be prepared by any of the methods well known in the art of pharmacy. Such methods include the step of bringing into association the coagulation factor complex with the carrier that constitutes one or more accessory ingredients. In general the formulations are prepared by uniformly and intimately bringing into association the active ingredient with liquid carriers or finely divided solid carriers or both, and then, if necessary, shaping the product.

Kits

Also disclosed herein are kits comprising the coagulation factor complexes. Formulations or compositions of the invention may be packaged together with, or included in a kit with, instructions or a package insert referring to the extended shelf-life of the coagulation factor complex. For instance, such instructions or package inserts may address recommended storage conditions, such as time, temperature and light, taking into account the extended or prolonged shelf-life of the coagulation factor complexes of the invention. Such instructions or package inserts may also address the particular advantages of the coagulation factor complexes of the inventions, such as the ease of storage for formulations that may require use in the field, outside of controlled hospital, clinic or office conditions. As described above, formulations of the invention may be in aqueous form and may be stored under less than ideal circumstances without significant loss of therapeutic activity.

Methods of Treating

The coagulation factor complexes and/or polynucleotides of the invention may be administered alone or in combination with other therapeutic agents. They may be administered in combination with other coagulation factor complexes and/or polynucleotides of the invention. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In specific aspects, coagulation factor complex used in methods of the present invention can be contained in a formulation containing a buffer, a sugar and/or a sugar alcohol (including without limitation trehalose and mannitol), a stabilizer (such as glycine), and a surfactant (such as Polysorbate 80). In further embodiments, the formulation may further include sodium, histidine, calcium, and glutathione.

In one aspect, the formulations comprising the coagulation factor complex are lyophilized prior to administration. Lyophilization is carried out using techniques common in the art and should be optimized for the composition being developed (Tang et al., Pharm Res. 21: 191-200, (2004) and Chang et al, Pharm Res. 13:243-9 (1996).

Methods of preparing pharmaceutical formulations can include one or more of the following steps: adding a stabilizing agent as described herein to said mixture prior to lyophilizing, adding at least one agent selected from a bulking agent, an osmolality regulating agent, an d a surfactant, each of which as described herein, to said mixture prior to lyophilization. A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration (Chen, Drug Development and Industrial Pharmacy, 18: 131 1-1354 (1992)).

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia: dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyl-eneoxycetanol, or condensation products of ethylene oxide with partial esters derived from fatty acids and a hexitol such as polyoxyethylene sorbitol monooieate, or condensation products of ethylene oxide with partial esters derived from fatty acids and hexitol anhydrides, for example and without limitation, polyethylene sorbitan monooieate. In various aspects, the aqueous suspensions also contain one or more preservatives, for example and without limitation, ethyl, or n-propyl, p-hydroxybenzoate.

In certain embodiments, compositions of the present invention are liquid formulations for administration with the use of a syringe or other storage vessel. In further embodiments, these liquid formulations are produced from lyophilized material described herein reconstituted as an aqueous solution. In a further aspect, the compositions of the invention further comprise one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

Single or multiple administrations of coagulation factor complexes are carried out with the dose levels and pattern being selected by the treating physician. For the prevention or treatment of disease, the appropriate dosage depends on the type of disease to be treated, the severity and course of the disease, whether drug is administered for preventive or therapeutic purposes, previous therapy, the patient's clinical history and response to the drug, and the discretion of the attending physician.

In further embodiments and in accordance with any of the above, treatment of coagulation diseases such as Hemophilia A may involve an initial treatment of coagulation factor complex alone or in combination with another agent, followed by one or more repeat doses of coagulation factor complex and/or other agents. The nature of the initial and then the subsequent repeat administrations will depend in part on the disease being treated.

In further aspects, coagulation factor complex can be administered to a subject in doses ranging from 0.5 IU/kg-200 IU kg. In some embodiments, coagulation factor complex is administered in doses ranging from 1-190, 5-180, 10-170, 15-160, 20-450, 25-140, 30-130, 35-120, 40-110, 45-100, 50-90, 55-80, or 60-70 IU/kg. In further embodiments and in accordance with any of the above, coagulation factor complex can be administered to a subject at doses of between about 1 IU/kg to about 150 IU/kg. In still further embodiments, the coagulation factor complex is administered at doses of between 1.5 IU/kg to 150 IU/kg, 2 IU/kg to 50 IU/kg, 5 IU/kg to 40 IU/kg, 10 IU/kg to 20 IU/kg, 10 IU/kg to 100 IU kg, 25 IU/kg to 75 IU/kg, and 40 IU kg to 75 IU/kg. In still further embodiments, coagulation factor complex is administered at 2, 5, 7.5, 10, 15, 20, 25, 30, 35, 40, 45, or 50 IU/kg. As will be appreciated and as is discussed further herein, appropriate dosages of coagulation factor complex may be ascertained through use of established assays for determining blood level dosages in conjunction with appropriate dose-response data.

In certain examples, the complexes of the current invention can be infused or administered to the muscle to treat hemophilia A. Compositions of coagulation factor complex can be contained in pharmaceutical formulations, as described herein. Such formulations can be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

In one aspect, formulations of the invention are administered by an initial bolus followed by a continuous infusion to maintain therapeutic circulating levels of drug product. As another example, the inventive compound is administered as a one-time dose. Those of ordinary' skill in the art will readily optimize effective dosages and administration regimens as determined by good medical practice and the clinical condition of the individual patient. The route of administration can be, but is not limited to, by intravenous, intraperitoneal, subcutaneous, or intramuscular administration. The frequency of dosing depends on the pharmacokinetic parameters of the agents and the route of administration. The optimal pharmaceutical formulation is determined by one skilled in the art depending upon the route of administration and desired dosage, See for example, Remington's Pharmaceutical Sciences, 18th Ed., 1990, Mack Publishing Co., Easton, Pa. 18042 pages 1435-1712, the disclosure of which is hereby incorporated by reference in its entirety for ail purposes and in particular for ail teachings related to formulations, routes of administration and dosages for pharmaceutical products. Such formulations influence the physical state, stability, rate of in vivo release, and rate of in vivo clearance of the administered agents. Depending on the route of administration, a suitable dose is calculated according to body weight, body surface area or organ size, Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. By way of example, a typical dose of coagulation factor complex of the present invention is approximately 50 IU/kg, equal to 500 μg/kg. As studies are conducted, further information will emerge regarding the appropriate dosage levels and duration of treatment for various diseases and conditions.

In some embodiments, coagulation factor complex is administered to a subject alone. In some embodiments, coagulation factor complex is administered to a subject in combination with one or more other coagulation factors.

In further embodiments, coagulation factor complex is administered to a subject no more than once daily. In further embodiments, coagulation factor complex is administered to a subject: no more than once every other day, no more than once every third day, no more than once every fourth day, no more than once every fifth day, no more than once a week, no more than once every two weeks, no more than once a month. In still further embodiments, coagulation factor complex is administered to a subject no more than twice a day.

Having generally described the invention, the same will be more readily understood by reference to the following examples, which are provided by way of illustration and are not intended as limiting.

Without further description, it is believed that one of ordinary skill in the art can, using the preceding description and the following illustrative examples, make and utilize the alterations detected in the present invention and practice the claimed methods. The following working examples therefore, specifically point out preferred embodiments of the present invention, and are not to be construed as limiting in any way the remainder of the disclosure.

EXAMPLES

Modifying the coagulation factors—Both FVIII and FVIIa are heavily studied and modified molecules because of their role in the treatment of hemophilia A. Several methods and sites on the proteins are available for modification. Wakabayashi, et al. (Wakabayashi, Koszelak, Mastri, & Fay, 2001) modified FVIII with acrylodan and fluorescein at Cys310 and Cys692 and demonstrated that this had no effect on the activity of FVIII in two different assays of FVIII activity. Purified FVIII can be reacted with maleimide compounds for one hour at room temperature or at 4° C. overnight in aqueous buffer. Maleimide reacts specifically with free cysteines and is widely used for protein labelling experiments. Labelled protein may then be isolated via ion exchange chromatography as described (Wakabayashi & Fay, 2013).

Another method to modify FVIII or FVIIa is to attach the desired molecule to the carbohydrate chains that modify each protein (Stennicke et al., 2013). A third method to modify either molecule is to attach a desired amino acid target to either end of the protein (Pasut & Veronese, 2012).

Albumin is known to bind a wide variety of small molecules including bilirubin, indomethacin, ibuprofen, etc. (Peters, 1995). The binding of most of these ligands is not pH dependent and so can be substituted for the fatty acid moiety at the end of the maleimide-polyethylene spacer.

Construction of the Albumin fusion proteins—The nucleotide sequence of the D'D3 fragment of human vWF or the soluble form of TF can be obtained from Genbank. A plasmid is then constructed containing the coding sequences and an appropriate length amino acid linker. These sequences can be flanked by appropriate DNA from the human albumin gene such that the construct can be inserted, in phase, at nucleotide 111 from the cap site into the human albumin gene in C3A, a human liver cell line (Kelly & Sussman, 2000). This can be accomplished using Cas/CRISPR, as described (Ran et al., 2013). Additionally, a plasmid containing the appropriate sequences can be synthesized de novo.

Purification of the Albumin fusion protein—The fusion protein can be recovered from C3A cell supernate using agarose beads conjugated with a monoclonal antibody to human serum albumin. The fusion protein can then be eluted with human serum albumin and separated by size selective chromatography.

Formation of the modified coagulation factor complex—The fusion protein can be incubated at 4° C. overnight with a limiting concentration of modified FVIII, then purified using size selective chromatography. Similarly, the TF—albumin fusion can be incubated at 4° C. overnight with a limiting concentration of the derivatized FVIIa, then purified using size selective chromatography.

In Vivo and In Vitro Characterization—In vivo and in vitro characterization of the activity, pharmacokinetics and pharmacodynamics of the therapeutic complex can be carried out as described (Mei et al., 2010; Yee et al., 2014). Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Materials and Methods

Purified, B deleted recombinant Factor VIII (FVIII) was purchased from RayBiotech (Norcross, Ga.). FVIII activity was assayed using the Coamatic FVIII assay obtained from Diapharma (West Chester Township, Ohio). FVIII ELISA was obtained from Affinity Biologicals (Ancaster, ON, CA). Other antibodies and ELISA kits were obtained from Abcam (Cambridge, Mass.). Fatty acid containing maleimide-PEG derivatives were synthesized by Creative PEGWorks (Chapel Hill, N.C.). Other maleimide-PEG derivatives were obtained from Nanocs (New York, N.Y.) or from Click Chemistry Tools (Scottsdale, Ariz.). Cell culture, molecular biology and general reagents were obtained from Life Technologies (Carlsbad, Calif.) or SigmaAldrich (St. Louis, Mo.). Column chromatography supplies and equipment were obtained from GE Lifesciences (Pittsburgh, Pa.).

Synthesis of CM110 and CM210-Expression plasmids for the synthetic genes CM110 and CM210 were synthesized by the Gene Art division of Life Technologies. The proteins were produced by polyethyleneimine (PEI) based transfection of C3A cells using a 6/1 ratio of PEI to DNA in medium containing 5% defined calf serum. After 24 hours, the medium was changed to serum free DMEM containing Glutamax. Medium was changed and collected every day for four days. Supernatant medium was passed over a 1 ml HisTRAP column, wash with ten column volumes of buffer containing 20 mM potassium phosphate, pH 7.4, 0.5 M NaCl and 30 mM imidazole. Protein was eluted from the column with the same buffer containing 300 mM imidazole. Protein containing fractions were pooled and concentrated, then changed into buffer containing 20 mM HEPES, pH 7.4, 150 mM NaCl, 4 mM $CaCl_2$, 0.01% Tween 20, by passage over gel filtration spin columns. The protein solution was then applied to a 10×300 mm Superdex 200 Increase column, run at 0.5 ml/min in the same buffer on an Akta Pure chromatography apparatus. Protein containing fractions were pooled and concentrated.

Modification of FVIII or CM210—Factor VIII was modified with a variety of molecules of the general structure maleimide—PEGn-X, where X was biotin, fluorescein isothiocyanate, laurate, myristate, transcyclooctene or methyl tetrazine. Factor VIII was dissolved in buffer containing 20 mM HEPES, pH 7.4, 150 mM NaCl and 4 mM $CaCl_2$, 0.01% Tween 20 then incubated for one hour at room temperature with 10 µM maleimide-PEG-X reagent. Excess reagent was removed by passage over either gel filtration spin columns for the smaller PEG compounds or over Superdex 200 Increase for the PEG reagents over 1000 daltons. CM110 or CM210 were derivatized with mal-PEG-TCO using the same conditions.

Complex formation—The FVIII/CM110 or CM210 complexes were formed by incubating modified FVIII with a ten-fold excess of CM110 or CM210 at room temperature for one hour in buffer containing 20 mM HEPES, pH 7.4, 150 mM NaCl and 4 mM $CaCl_2$. Complexes were purified by chromatography over either Superdex 200 Increase or Superose 6 Increase in the same buffer at 0.5 ml/min.

For covalent complex formation FVIII modified with maleimide-PEG4-MeTetrazine was incubated with a ten-fold excess of maleimide-PEG3-TCO modified CM110 or CM210 in buffer containing 20 mM HEPES, pH 7.4, 150 mM NaCl and 4 mM CaCl2 at 4° C. overnight. Complexes were isolated by passage over Superose 6 Increase.

REFERENCES

Andersen, J. T., Pehrson, R., Tolmachev, V., Daba, M. B., Abrahmsén, L., & Ekblad, C. (2011). Extending half-life by indirect targeting of the neonatal Fc receptor (FcRn) using a minimal albumin binding domain. The Journal of Biological Chemistry, 286(7), 5234-5241.

Bradbury, A. R. M., Sidhu, S., Dübel, S., & McCafferty, J. (2011). Beyond natural antibodies: the power of in vitro display technologies. Nature Publishing Group, 29(3), 245-254.

Buyue, Y., Liu, T., Kulman, J. D., Toby, G. G., Kamphaus, G. D., Patarroyo-White, S., et al. (2014). A Single Chain Variant of Factor VIII Fc Fusion Protein Retains Normal In Vivo Efficacy but Exhibits Altered In Vitro Activity. PLoS ONE, 9(11), e113600.

Ginn, C., Khalili, H., Lever, R., & Brocchini, S. (2014). PEGylation and its impact on the design of new protein-based medicines. Future Medicinal Chemistry, 6(16), 1829-1846.

Hoots, W. K. (2003). Comprehensive care for hemophilia and related inherited bleeding disorders: why it matters. Current Hematology Reports, 2(5), 395-401.

Horisawa, K. (2014). Specific and quantitative labeling of biomolecules using click chemistry. Frontiers in Physiology 5, 457.

Kelly, J. H., & Sussman, N. L. (2000). A Fluorescent Cell-Based Assay for Cytochrome P-450 Isozyme 1A2 Induction and Inhibition. Journal of Biomolecular Screening, 5(4), 249-253.

Kempton, C. L., & Meeks, S. L. (2014). Toward optimal therapy for inhibitors in hemophilia. Hematology/the Education Program of the American Society of Hematology. American Society of Hematology. Education Program, 2014(1), 364-371.

Kramer, R. H., & Karpen, J. W. (1998). Spanning binding sites on allosteric proteins with polymer-linked ligand dimers. Nature, 395(6703), 710-713.

Lawson, J. H., Butenas, S., Ribarik, N., & Mann, K. G. (1993). Complex-dependent inhibition of factor VIIa by antithrombin III and heparin. The Journal of Biological Chemistry, 268(2), 767-770.

Lenting, P. J., Christophe, O. D., & Denis, C. V. (2015). von Willebrand factor biosynthesis, secretion, and clearance: connecting the far ends. Blood, 125(13), 2019-2028.

Mannucci, P. M., & Mancuso, M. E. (2014). Fc-fusion technology and recombinant FVIII and FIX in the management of the hemophilias. Drug Design, Development and Therapy, 365.

Mei, B., Pan, C., Jiang, H., Tjandra, H., Strauss, J., Chen, Y., et al. (2010). Rational design of a fully active, long-acting PEGylated factor VIII for hemophilia A treatment. Blood, 116(2), 270-279.

Oldenburg, J., & Albert, T. (2014). Novel products for haemostasis—current status. Haemophilia, 20, 23-28.

Orlova, N. A., Kovnir, S. V., Vorobiev, I. I., Gabibov, A. G., & Vorobiev, A. I. (2013). Blood Clotting Factor VIII: From Evolution to Therapy. Acta Naturae, 5(2), 19-39.

Pasut, G., & Veronese, F. M. (2012). State of the art in PEGylation: The great versatility achieved after forty years of research. Journal of Controlled Release, 161(2), 461-472.

Peters, T., Jr. (1995). All about albumin: biochemistry, genetics, and medical applications.

Philips, J.-C., & Scheen, A. (2006). Insulin detemir in the treatment of type 1 and type 2 diabetes. Vascular Health and Risk Management, 2(3), 277-283.

Pipe, S. W. (2010). Hemophilia: new protein therapeutics. Hematology/the Education Program of the American Society of Hematology. American Society of Hematology. Education Program, 2010, 203-209.

Ran, F. A., Hsu, P. D., Lin, C.-Y., Gootenberg, J. S., Konermann, S., Trevino, A. E., et al. (2013). Double Nicking by RNA-Guided CRISPR Cas9 for Enhanced Genome Editing Specificity. Cell, 1-15.

Schulte, S. (2008). Use of albumin fusion technology to prolong the half-life of recombinant factor VIIa. Thrombosis Research, 122(S4), S14-S19.

Smith, S. A., Travers, R. J., & Morrissey, J. H. (2015). How it all starts: Initiation of the clotting cascade. Critical Reviews in Biochemistry and Molecular Biology, 1-11.

Srivastava, A., Brewer, A. K., Mauser-Bunschoten, E. P., Key, N. S., Kitchen, S., Llinas, A., et al. (2012). Guidelines for the management of hemophilia. Haemophilia, 19(1), e1-e47.

Stennicke, H. R., Kjalke, M., Karpf, D. M., Balling, K. W., Johansen, P. B., Elm, T., et al. (2013). A novel B-domain O-glycoPEGylated FVIII (N8-GP) demonstrates full efficacy and prolonged effect in hemophilic mice models. Blood, 121(11), 2108-2116.

Vadivel, K., & Bajaj, S. P. (2012). Structural biology of factor VIIa/tissue factor initiated coagulation. Frontiers in Bioscience: a Journal and Virtual Library, 17, 2476-2494.

van der Flier, A., Liu, Z., Tan, S., Chen, K., Drager, D., Liu, T., et al. (2015). FcRn Rescues Recombinant Factor VIII Fc Fusion Protein from a VWF Independent FVIII Clearance Pathway in Mouse Hepatocytes. PLoS ONE, 10(4), e0124930-23.

Wakabayashi, H., & Fay, P. J. (2013). Molecular orientation of Factor VIIIa on the phospholipid membrane surface determined by fluorescence resonance energy transfer. The Biochemical Journal, 452(2), 293-301.

Wakabayashi, H., Koszelak, M. E., Mastri, M., & Fay, P. J. (2001). Metal Ion-independent Association of Factor VIII Subunits and the Roles of Calcium and Copper Ions for Cofactor Activity and Inter-Subunit Affinity t. Biochemistry, 40(34), 10293-10300.

Yee, A., Gildersleeve, R. D., Gu, S., Kretz, C. A., McGee, B. M., Carr, K. M., et al. (2014). A von Willebrand factor fragment containing the D'D3 domains is sufficient to stabilize coagulation factor VIII in mice. Blood, 124(3), 445-452.

Zhou, H.-X. (2006). Quantitative Relation between Intermolecular and Intramolecular Binding of Pro-Rich Peptides to SH3 Domains. Biophysical Journal, 91(9), 3170-3181.

What is claimed is:

1. A coagulation factor complex comprising:
   a. a coagulation factor;
   b. a fusion protein comprising a first protein fused to albumin or an albumin fragment; and
   c. a modifying molecule, wherein the modifying molecule is coupled to the coagulation factor in such a way as to allow binding by the fusion protein, thereby creating a modified coagulation factor, wherein the modifying molecule is attached to the coagulation factor through at least one bond that is not a peptide bond;
wherein the modified coagulation factor and the fusion protein interact in at least two independent sites.

2. The coagulation factor complex of claim 1, wherein at least one binding site of the modified coagulation factor is a natural binding site.

3. The coagulation factor complex of claim 1, wherein at least one binding site of the fusion protein is provided by the modifying molecule.

4. The coagulation factor complex of claim 1, wherein the coagulation factor is Factor VIII.

5. The coagulation factor complex of claim 1, wherein the first protein of the fusion protein is a fragment of von Willebrand's factor.

6. The coagulation factor complex of claim 5, wherein the fragment of von Willebrand's factor is a D'D3 fragment.

7. The coagulation factor complex of claim 1, wherein the modified coagulation factor and the fusion protein interact covalently.

8. The coagulation factor complex of claim 7, wherein the covalent bond is not a peptide bond.

9. The coagulation factor complex of claim 7, wherein the covalent bond is not a peptide bond produced by translation of a nucleic acid.

10. The coagulation factor complex of claim 1, wherein the modifying molecule comprises a fatty acid.

11. The coagulation factor complex of claim 1, wherein the modifying molecule is attached to the coagulation factor through a polyethylene glycol chain.

12. The coagulation factor complex of claim 11, wherein the polyethylene glycol chain is linked to a maleimide on the coagulation factor.

13. The coagulation factor complex of claim 12, wherein the polyethylene glycol chain is linked to maleimide with a structure comprising maleimide-$PEG_N$-X, wherein this X is methyl tetrazine.

14. The coagulation factor complex of claim 1, wherein the first protein of the fusion protein is joined together with albumin via a linker.

15. The coagulation factor complex of claim 1, wherein the coagulation factor comprises modified amino acids.

16. The coagulation factor complex of claim 1, wherein the fusion protein comprises modified amino acids.

17. The coagulation factor complex of claim 1, wherein half-life of the coagulation factor complex is at least 20% greater compared to the coagulation factor alone.

18. A kit comprising the coagulation factor complex of claim 1.

19. A method of treating a subject with a disease requiring coagulation factor infusion, the method comprising administering to the subject the coagulation factor complex of claim 1.

20. The method of claim 19, wherein the administration of the coagulation factor complex to the subject results in a blood level half-life of the coagulation factor complex which is greater than the blood level half-life obtained upon administration of the coagulation factor alone.

21. A coagulation factor complex comprising:
   a. a coagulation factor;
   b. a fusion protein comprising a first protein fused to albumin or an albumin fragment; and
   c. a modifying molecule, wherein the modifying molecule is coupled to the coagulation factor in such a way as to allow binding by the fusion protein, thereby creating a modified coagulation factor, wherein the modifying molecule is attached to the coagulation factor through a polyethylene glycol chain;
   wherein the modified coagulation factor and the fusion protein interact in at least two independent sites.

22. The coagulation factor complex of claim 21, wherein the coagulation factor is Factor VIII.

23. The coagulation factor complex of claim 21, wherein the first protein of the fusion protein is a fragment of von Willebrand's factor.

* * * * *